United States Patent [19]

Zengel et al.

[11] 4,057,588

[45] Nov. 8, 1977

[54] PROCESS FOR THE PREPARATION OF PHLOROGLUCINOL

[75] Inventors: Hans-Georg Zengel, Kleinwallstadt; Manfred Bergfeld, Erlenbach, Main, both of Germany

[73] Assignee: Akzona Incorporated, Asheville, N.C.

[21] Appl. No.: 651,089

[22] Filed: Jan. 21, 1976

[30] Foreign Application Priority Data

Jan. 22, 1975 Germany .............................. 2502429

[51] Int. Cl.² .............................................. C07C 39/10
[52] U.S. Cl. .............................. 260/621 R; 260/625; 260/553 A; 260/558 R
[58] Field of Search ............... 260/625, 621 R, 623 H, 260/553 A, 558 R

[56] References Cited

U.S. PATENT DOCUMENTS

| 3,230,266 | 1/1966 | Baldoni ............................ 260/621 R |
| 3,929,907 | 12/1975 | Janzon et al. ..................... 260/619 R |
| 3,931,340 | 1/1976 | Nishihira et al. ................ 260/623 H |
| 3,932,538 | 1/1976 | Obara et al. ......................... 260/625 |

FOREIGN PATENT DOCUMENTS 1,012,782  12/1965  United Kingdom ................ 260/625

Primary Examiner—Bernard Helfin
Assistant Examiner—W. B. Lone
Attorney, Agent, or Firm—Francis W. Young; Robert F. Green

[57] ABSTRACT

Phloroglucinol is prepared by chlorinating benzene-tricarboxylic acid-(1,3,5)-triamide in an aqueous, inorganic acid medium to form benzene-tricarboxylic acid-(1,3,5)-tri-N-chloramide, which is a new compound; the latter is converted by treatment with ammonia into 1,3,5-triureido-benzene, which is hydrolyzed in inorganic acid solution to phloroglucinol.

8 Claims, No Drawings

PROCESS FOR THE PREPARATION OF PHLOROGLUCINOL

BACKGROUND OF THE INVENTION

The invention relates to a novel process for the preparation of phloroglucinol (1,3,5-trihydroxybenzene) from benzene tricarboxylic acid-(1,3,5)-triamide.

Several sntheses of phloroglucinol are known. Especially important from a technical standpoint is the reduction of 1,3,5-trinitrobenzene to 1,3,5-triaminobenzene and subsequent hydrolysis of the latter. According to earlier processes, the reduction can be carried out with tin in hydrochloric acid solution (Weidel and Pollak, Monatsh. 21,15, (1900); Hepp, Ann. 215, 348; Organic Synthesis Coll. Vol. I, 444 (1932); US-P 2 461 498) or with hydrogen and Raney nickel in an organic solvent, especially ethylacetate (WG-P 813 709; Gill et al., J. Chem. Soc., 1753 (1949); GB P 1 106 088). Iron/hydrochloric acid is a suitable reduction agent for large-scale reduction of trinitrobenzene (US P 2 614 126; Kastens, Ind. and Engin. Chem. 42, 402 (1950); GB P 1 022 733). Platinum, palladium and rhodium catalysts have also been suggested for the reduction of trinitrobenzene (FR. P 1 289 647; Desseigne, Mem. Poudras 44, 325 (1962). For this synthesis instead of 1,3,5 trinitrobenzene one can also use 2,4,6.-trinitrobenzoic acid, which on a large-scale can be obtained by oxidation of trinitrotoluene with sodium dichromate in sulfuric cid (Kastens, 1.c.), since the 2,4,6-triaminobenzoic acid obtained in the reduction is either immediately decarboxylated to triaminobenzene or is converted to phloroglucinol in the subsequent hydrolysis (GB P 1 022 733; GB P 1 106 088; GB P 1 274 551). It is furthermore known to use 5-nitro-1,3-diaminobenzene insteand of trinitrobenzene (GB P 1 012 782). Hydrolysis of triamine to phloroglucinol is normally carried out in an inorganic acid solution (Flesch, Monatsh. 18, 755 (1897); WG P 102 358), and according to a more recent process in the presence of copper and/or its salts as catalyst (WG P 1 195 327).

Phloroglucinol can also be prepared by an interesting large-scale process by oxidation of 1,3,5-triisopropylbenzene, separation of trihydroperoxide from the mixture of mono-, di- and trihydroperoxide with subsequent ketonic cleavage of the latter (GB P 751 598; EG P 12 239; Seidel et al; Journ. prakt. Chemie 275, 278 (1956). It is also possible to oxidize triisopropylbenzene with oxygen in acetic acid anhydride directly to phloroglucinol triacetate and to hydrolyze the latter with alcoholic sodium hydroxide to phloroglucinol (US P 2 799 698). One can also start from m-isopropylresorcinol, esterifying the latter with acetic acid annhydride, oxidizing the resulting m-isopropylresorcinol-diacetate to hydroperoxide and finally react the latter with acid to phloroglucinol (US P 3 028 410).

Phloroglucinol can furthermore be obtained by melting resorcinol (Barth and Schreder, Ber. 12, 503 (1879), chlorine or bromine substituted resorcinol in the 2-,4-, 5-, 3,5- or 2,4-position (WG P 2 231 005) or 1,3,5-benzenetrisulfonic acid (US P 2 773 908) with excess alkali hydroxide.

Apart from the cited benzene derivatives, hexoxybenzene, picryl chloride, tetrachlorobenzene and tetrabromobenzene as well as tribromobenzene, were mentioned as initial materials for the synthesis of phloroglucinol; hexaoxybenzene is hydrated in aqueous medium with platinum oxide (Kuhn et al., Ann. 565, 1 (1949), picryl chloride is reduced with tin and hydrochloric acid or electrolytically with subsequent hydrolyzation of the resulting 1,3,5-triaminobenzene or 2,4,6-triamino-1-chlorobenzene (Heertjes, Recueil 78, 452 (1959). The cited tetrahalobenzenes are ammonolyzed in the presence of a copper catalyst and the intermediate triamine is hydrolyzed without prior separation in the reaction mix (US P 3 230 266). Tribromobenzene can be reacted with sodium methanolate and catalytic amounts of Cu iodide in methanol/dimethylformamide as solvent to 1,3,5-trimethoxybenzene, which is finally also hydrolyzed (McKillop et al., Synthetic Communications 4(1)→, 35 (1974).

It is also known to synthesize phloroglucinol using diethyl malonate as starting material; when treated with metallic sodium there is a spontaneous condensation of diethyl malonate to the trisodium salt of phloroglucinol-di-carboxylic acid diethylester, this intermediate product is subsequently subjected to alkaline hydrolysis and decarboxylation (v. Baeyer, Ber. 18, 3454 (1885); Willstaetter, Ber. 32, 1272 (1899); Leuchs, Ber. 41, 3172 (1908); Kominos, Bull. Soc. Chim. Fr. 23, 449 (1918). This synthesis was improved to the extent that sodium diethyl malonate and trisodium salt of phloroglucinol dicarboxylic acid diethylester is obtained in a single step by boiling in a neutral solvent of high BP, preferably Dekalin (EG P 24 998).

Among the above-mentioned processes, only the process based on 2,4,6 trinitrobenzoic acid ester, has obviously so far found acceptance in the art. This process has, however, a number of serious drawbacks. 2,4,6-trinitrobenzoic acid is obtained by oxidation of explosive trinitrotoluene, hence the process is dangerous. Moreover, the total yield, based on 2,4,6-trinitrobenzene via trinitrobenzene, triaminobenzene to phloroglucinol, is very small. The process also has drawbacks because of the waste water problem: the waste water of the oxidation and reduction reactions is highly acid, contains heavy metal chromium and/or iron and requires processing.

GENERAL DESCRIPTION OF THE INVENTION

The present invention relates to a process which is also suitable for large-scale preparation of phloroglucinol, but without the drawbacks of the known industrial process.

The object of the present invention is a process for the preparation of phloroglucinol, characterized in that benzene tricarboxylic acid-(1,3,5)-triamide is chlorinated in an aqueous inorganic acid medium, and the resulting benzene-tricarboxylic acid-(1,3,5)-tri-N-chloramide is reacted by treatment with ammonia to form 1,3,5-triureido-benzene, followed by hydrolysis in inorganic acid solution to phloroglucinol.

Benzene-tricarboxylic acid-(1,3,5)-triamide is a known compound which is obtained, e.g. from benzene tricarboxylic acid-(1,3,5)-trichloride by treatment with aqueous ammonia (Bennett and Wain, Soc. 1936, 1108) or by heating of 1,3,5-benzenetricarboxylic acid (trimesic acid) with sulfamide (Kirssanov and Abrashovna, Chem. Zentralbl. 1956. 11966). Benzene tricarboxylic acid is prepared on a large scale, and is obtained by oxidation of mesitylene which, being a primary petrochemical product, is available in large quantities or is obtained synthetically by condensation of acetone in concentrated sulfuric acid.

Benzene-tricarboxylic acid-(1,3,5)-tri-N-chloramide according to the invention is a new compound of the formula:

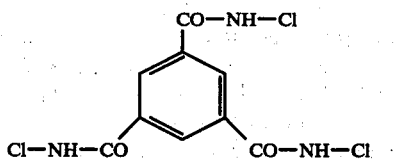

It is obtained, in accordance with the present invention, by chlorination of the triamide in aqueous inorganic acid medium. Chlorination is carried out preferably in aqueous or aqueous-alcoholic medium. Suitable inorganic acids are hydrochloric acid, sulfuric acid and phosphoric acid. The inorganic acid solutions are used as 2 to 26 wt.% solutions. A neutral, aqueous suspension of triamide can also be used, in which case hydrogen chloride formed as byproduct of chlorination is dissolved in the reaction mix and the reaction thus takes place in dilute, aqueous hydrochloric acid medium. Higher yields of tri-N-chloramide are obtained when chlorination is carried out in a mixture of dilute inorganic acid and an alcohol, preferably methanol or ethanol. Especially good results are obtained with a mixture of aqueous hydrochloric acid and methanol. The ratio of aqueous inorganic acid to alcohol is preferably within the range of 60:40 to 40:60.

Chlorination of the acid amide is exothermic. It is performed at temperatures of 0° to 40° C. Higher temperatures present a drawback inasmuch as under these conditions hydrolysis and chlorination of the nucleus take place as secondary reaction. Chlorination is preferably performed at 5°0 to 30° C, whereby the reaction heat can be controlled by water cooling.

Chlorination can be performed at normal pressure as well as at increased pressure. With increasing pressure, there is a reduction in reaction time, but for reasons of economy, a pressure range between 1 and 10 atm. is preferred.

Since chlorination according to the invention takes place in heterogeneous phase, proper mixing of the suspension is required. The dilution of the reaction mix should be such as to allow stirring or any other type of mixing without difficulty. The preferred dilution of the reaction mix is about 100 – 300 g triamide per liter of water, aqueous inorganic acid or water/ alcohol mixture.

Under the present conditions, chlorination is completed after about 0.3 to 5 hours. Conversion of triamide to tri-N-chloramide is practically quantitative, without interim formation of a solution. The suspension obtained after completed chlorination contains only tri-N-chloramide as solid. The latter can be separated very simply e.g by filtration or centrifuging. After washing e.g. with cold water and drying at e.g. 70° C in vacuum, tri-N-chloramide of the highest purity is obtained.

Like the triamide, 1,3,5-triureido benzene is also known. It is obtained from 1,3,5-triisocyanato-benzene with ammonia in ether (Gill et al., Soc. 1949, 1753; WG P 815 486). With the process according to the invention it is formed by treatment of benzene tricarboxylic acid-(1,3,5)-tri-N-chloramide with ammonia. Expediently, tri-N-chloramide is suspended in water, reacted with ammonia in the presence of cooling, followed by vigorous mixing of the reaction mixture. The reaction mixture should thereby never exceed a temperature of 25° C. Once the sediment is fully dissolved, the solution is quickly heated to the boil and kept at this temperature for about 15 to 30 min. After cooling, the precipitated 1,3,5-triuredio-benzene is filtered off, washed and dried. At least stoichiometric quantities of ammonia are used hereby, i.e. one mole benzene tricarboxylic acid-(1,3,5)-tri-N-chloramide requires 6 moles of ammonia. It is advantageous to use up to 10 mole % excess ammonia and after separation of 1,3,5-triureido-benzene to use the filtrate for the reaction of additional tri-N-chloramide. The yield in this process step exceeds 97% of the theory.

For the preparation of phloroglucinol according to the invention, 1,3,5-triureido-benzene is hydrolyzed in inorganic acid solution. Suitable inorganic acids are hydrochloric acid and sulfuric acid. The inorganic acid is used preferably in dilute form and in quantities of 6 to 8 moles per mole of triureido-benzene. Hydrolysis is carried out at temperatures from 140° to 200° C and corresponding characteristic partial pressures. Reaction time is some 5 to 20 hours. Phloroglucinol is separated e.g. by cooling and drying the solution obtained during hydrolysis. The solid is essentially composed of phloroglucinol, but may contain as much as 15 wt.% phloroglucidol. In large-scale production of phloroglucinol by the process according to the invention, scarcely soluble phloroglucidol is separated from the still hot hydrolsis mixture by filtration. Phloroglucinol crystallizes during cooling of the filtrate and can then be separated by filtration or centrifuging.

The process according to the invention is eminently suited for large-scale production of phloroglucinol. In contrast to the known process the initial material used is not explosive. Moreover, high yields are obtained in all process steps, the total yield being thus higher than for the known process. The waste water is not highly acid nor does it contain heavy metals and thus this process is ecologically more favorable than the known process.

Phloroglucinol is used as developer in the diazotype process, and as a cross-linking, vulcanizing, stabilizing, and anti-corrosion agent, as well as a developing component in the preparation of numerous dyes. In the laboratory it is used as a reagent for aldehydes, pentoses, lignin, galactoses and other substances. Furthermore, it is used in the preparation of coumarins and flavonols, and of pharmaceuticals.

DESCRIPTION OF THE PREFERRED EMBODIMENTS

The process according to the invention is illustrated in greater detail in the following examples, which are not to be considered as limiting the invention thereto:

EXAMPLE 1

Preparation of Benzene-tricarboxylic acid-(1,3,5)-tri-N-chloramide a. 20.7 g (0.1 mole) finely pulverized benzene-tricarboxylic acid-(1,3,5)-triamide was suspended in a 1-liter glass autoclave with gas inlet tube in 350 ml 5% HCl under vigorous stirring and for 2 hours a stream of chlorine at 26° C and a pressure of 6 atm. was passed through the suspension at the rate if 2 l/hour. After completed reaction, the reaction product was filtered off and neutralized by washing. After drying at 40° C under vacuum the yield was 30.2 g of a white powder composed of 27.8 g (89.7% of the theory) benzene tricarboxylic acid-(1,3,5)tri-N-chloramide and 2.4 g unreacted triamide. Under otherwise identical conditions but without pressure the yield was 25.3 g (= 81.5% of the theory) tri-N-chloramide. Chlorination is > 98% selective.

b. 20.8 g (0.1 mole) benzene-tricarboxylic acid-(1,3,5)-triamide were suspended in a pressure column (glass) with gas inlet tube in a mixture of 180 ml 10% HCl and 180 ml methanol under vigorous stirring (magnetic stirrer) and as in a. above, chlorine at 25° C and a pressure of 6 atm. was passed through for 2 hours. After completed reaction the product was filtered off and processed as in a. above. After drying, the yield was 30.35 g of a colorless, fine white powder quantitatively composed of tri-N-chloramide, the yield being 97.7% of the theory of tri-N-chloramide.

EXAMPLE 2

Preparation of 1,3,5-triureido-benzene

A slurry is prepared from 19.2 g (62 mole) benzene-tricarboxylic acid-( 1,3,5)-tri-N-chloroamide in 100 ml water and after cooling to 5°- 10° C reacted with 300 ml. conc. ammonia under vigorous stirring. The gently exothermic reaction was controlled by external cooling so that the internal temperature rose to max. 25° C. After a clear solution was obtained (about 5–10 min after adding the ammonia) the system was quickly heated to the boil (15–30 min). After but a few minutes, a fine, white precipitate began to form, increasing rapidly in volume, but which on reaching the boiling point dissolved again noticeably.

After a total reaction time of 45 min. the mix was cooled and stored for 5 hrs in the refrigerator, after which the precipitate was removed by suction and washed with 25 ml ice water, twice. After drying, the yield was 15.26 g (60.5 moles) pure 1,3,5-triuredio benzene in the form of colorless, felted needles, being 97.5% of the theory.

EXAMPLE 3

Preparation of Phloroglucinol 10.1 (40 mmole) 1,3,5-triuredio-benzene was reacted with (11.3 g) 0.31 mole HCl = 31.5 g 36% hydrochloric acid (corresponding at the end of the reaction to an HCl excess of 2.5 g = 0.5% HCl solution) in a 1-liter autoclave lined with Teflon for 16 hours at 180° C and a characteristic partial pressure of 20 atm. under vigorous stirring.

After completed reaction, the system was cooled, evaporated and the light-brown, clear solution was dried by condensation. 19.1 g of an ocher to light-brown, readily pulverized solid was left behind. (The theoretical amount for 100% conversion to phloroglucinol and ammonium chloride is calculated at 19.35 1 g). 4.83 g of a mixture of phloroglucinol and phloroglucidol was isolated from the product mix by extraction with ethyl acetate, yielding after chromatographic separation 4.23 g (32 84.5% of the theory) phloroglucinol, whereas 12.2% of the originally formed phloroglucinol had been converted to phloroglucidol. Hence, the selectivity with respect to hydrolysis of the 1,3,5-triureido-benzene to phloroglucinol was 96.7% of the theory.

After only 10 hours of reaction, but otherwise unchanged conditions and identical processing, the same system yielded 71.2% phloroglucinol and 3.1% phloroglucidol, and after a 5-hr reaction b 55.3% phloroglucinol and 1.2% phloroglucidol.

What is claimed is:

1. A process for the preparation of phloroglucinol from benzene-tricarboxylic acid — (1,3,5) — triamide comprising the steps of:
   a. utilizing chlorine to chlorinate benzene — tricarboxylic acid — (1,3,5) — triamide in an aqueous inorganic acid medium selected from the group consisting of aqueous hydrochloric acid, aqueous sulfuric acid, and aqueous phosphoric acid, an aqueous alcoholic medium, or a mixture thereof, at a temperature from about 0° to about 40° C, to form benzene — tricarboxylic acid(1,3,5) — tri-N-chloramide;
   b. reacting an aqueous suspension of said tri-N-chloramide with ammonia at a temperature not exceeding 25° C until said tri-N-chloramide has dissolved and subsequently heating the reaction mixture to boiling to form 1,3,5-triureido-benzene; and
   c. hydrolyzing said 1,3,5-triureido-benzene in an inorganic acid solution selected from the group consisting of hydrochloric acid solution and sulfuric acid solution at a temperature from about 140° to about 200° C and corresponding characteristic partial pressure to form phloroglucinol.

2. The process of claim 1 in which the chlorination in step (a) is performed in aqueous-alcoholic medium.

3. The process of claim 1 in which the chlorination is performed in a mixture of aqueous hydrochloric acid and methanol.

4. The process of claim 1 in which the chlorination in step (a) is performed at a temperature in the range of 0° to about 30° C.

5. The process of claim 1 in which in step (b) the N-chloramide in the form of an aqueous slurry is reacted with ammonia under cooling and vigorous agitation of the reaction mixture.

6. The process of claim 1, in which the 1,3,5-triureido-benzene is hydrolyzed in step (c) with approximately a 6- to 8- fold molar amount of an inorganic acid.

7. The process of claim 1 in which the chlorination in step (a) is performed in an aqueous inorganic acid medium.

8. The process of claim 1 in which the chlorination in step (a) is performed in an aqueous inorganic acid/alcoholic medium.

* * * * *